US010692600B2

(12) United States Patent
Suzuki et al.

(10) Patent No.: US 10,692,600 B2
(45) Date of Patent: Jun. 23, 2020

(54) AUTOMATIC ANALYZER, REMOTE MAINTENANCE SYSTEM, AND MAINTENANCE METHOD

(71) Applicant: HITACHI HIGH-TECHNOLOGIES CORPORATION, Tokyo (JP)

(72) Inventors: Kentaro Suzuki, Tokyo (JP); Yasuo Kaneko, Tokyo (JP); Toshihide Hanawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/332,084

(22) PCT Filed: Sep. 15, 2017

(86) PCT No.: PCT/JP2017/033427
§ 371 (c)(1),
(2) Date: Mar. 11, 2019

(87) PCT Pub. No.: WO2018/056202
PCT Pub. Date: Mar. 29, 2018

(65) Prior Publication Data
US 2019/0206559 A1 Jul. 4, 2019

(30) Foreign Application Priority Data
Sep. 21, 2016 (JP) .................. 2016-183628

(51) Int. Cl.
*G08B 29/00* (2006.01)
*G16H 40/40* (2018.01)
(Continued)

(52) U.S. Cl.
CPC ............. *G16H 40/40* (2018.01); *G01N 35/00* (2013.01); *G01N 35/00871* (2013.01);
(Continued)

(58) Field of Classification Search
CPC .. G16H 40/40; G01N 35/00871; G01N 35/00; G01N 2035/009; G01N 2035/0091;
(Continued)

(56) References Cited

U.S. PATENT DOCUMENTS 6,078,649 A * 6/2000 Small ...................... H04M 11/04
379/39
7,147,827 B1 * 12/2006 Balisky .................. G05D 21/02
422/110
(Continued)

FOREIGN PATENT DOCUMENTS

JP 2001-250008 A 9/2001
JP 2005-195401 A 7/2005
(Continued)

OTHER PUBLICATIONS

International Search Report of PCT/JP2017/033427 dated Dec. 19, 2017.

*Primary Examiner* — Kerri L McNally
*Assistant Examiner* — Thang D Tran
(74) *Attorney, Agent, or Firm* — Mattingly & Malur, PC (57) ABSTRACT

It is an object to provide a system for a service department to contact a customer for improving customer service when it is determined that the customer has difficulty in handling an alarm by themselves in the case where the alarm is generated due to abnormality of an automatic analyzer and the automatic analyzer is deactivated. The automatic analyzer includes: a display to display an alarm screen; a computer that generates alarm generation information that indicates that an alarm has been generated due to abnormality and alarm deletion information that indicates that the customer has deleted the alarm displayed on the alarm screen based on the alarm generation information; and an information sharing portion that shares the alarm generation
(Continued)

information and alarm deletion information that are generated by the computer with an external alarm maintenance system.

12 Claims, 8 Drawing Sheets

(51) Int. Cl.
    *H04L 12/24*     (2006.01)
    *G08B 29/10*     (2006.01)
    *G01N 35/00*     (2006.01)
    *G08B 5/22*     (2006.01)

(52) U.S. Cl.
    CPC .............. *G08B 5/22* (2013.01); *G08B 29/10* (2013.01); *H04L 41/064* (2013.01); *H04L 41/069* (2013.01); *G01N 2035/009* (2013.01); *G01N 2035/0091* (2013.01)

(58) Field of Classification Search
    CPC ......... G08B 5/22; G08B 29/10; H04L 41/069; H04L 41/064
    USPC .......................................... 340/506
    See application file for complete search history.

(56) References Cited

U.S. PATENT DOCUMENTS

| | | | | |
|---|---|---|---|---|
| 2001/0043882 A1* | 11/2001 | Berger | ................... | G01N 35/00 422/67 |
| 2003/0097054 A1* | 5/2003 | Sasaki | ..................... | A61B 8/00 600/407 |
| 2005/0043014 A1* | 2/2005 | Hodge | .................... | H04M 1/67 455/411 |
| 2007/0255756 A1* | 11/2007 | Satomura | ......... | G01N 35/00663 |
| 2009/0210283 A1* | 8/2009 | Miyamoto | .......... | G06F 11/0748 705/7.14 |
| 2009/0214385 A1* | 8/2009 | Mori | ................ | G01N 35/00663 422/63 |
| 2009/0263281 A1* | 10/2009 | Ushiku | ............ | G01N 35/00603 422/68.1 |
| 2010/0146625 A1* | 6/2010 | Kawamura | ............ | G16H 10/40 726/24 |
| 2010/0287477 A1* | 11/2010 | Maetzler | ............. | G06F 3/04842 715/733 |
| 2011/0288692 A1* | 11/2011 | Scott | ....................... | G06F 21/55 700/297 |
| 2012/0180136 A1* | 7/2012 | Song | ..................... | H04L 63/083 726/26 |
| 2012/0239676 A1* | 9/2012 | Kaneko | ............ | G01N 35/00732 707/758 |
| 2013/0280130 A1* | 10/2013 | Sarwar | ............... | G01N 35/1002 422/63 |
| 2015/0029020 A1* | 1/2015 | Bailey | .................. | G08B 25/001 340/502 |
| 2015/0066782 A1* | 3/2015 | Vainberg | ................ | G06Q 10/20 705/305 |
| 2015/0100686 A1* | 4/2015 | Sakurai | ............... | H04L 43/0817 709/224 |
| 2016/0170686 A1* | 6/2016 | Haas | ..................... | G06F 3/1229 358/1.14 |

FOREIGN PATENT DOCUMENTS

| | | |
|---|---|---|
| JP | 2005-348928 A | 12/2005 |
| JP | 2011-203197 A | 10/2011 |

* cited by examiner

| | ALARM NO | ALARM LEVEL | ALARM CONTENT | ALARM GENERATION TIME |
|---|---|---|---|---|
| ☐ | 0005 | WARNING | LOW WASHING SOLUTION | YYYY/MM/DD:HH:MM:SS |
| ☑ | 0002 | EMERGENCY STOP | ANALYZER COVER OPENED | YYYY/MM/DD:HH:MM:SS |
| ☐ | 0023 | STOP | MECHANICAL ABNORMALITY OF REAGENT DISC | YYYY/MM/DD:HH:MM:SS |

201, 202, 203, 204, 205

ALARM HANDLING METHOD
× × × × × × × × × × × × × ×

207 / 215

[UPDATE ALARM] 208   [DELETE ALARM] 209   [CLOSE] 210

214

ANALYZER STATUS                                 2016/08/31

| MEASUREMENT RESULT | REAGENT | ALIBRATION | ACCURACY MANAGEMENT | UTILITY |

[STOP]
[DISPLAY ALARM SCREEN] — 212
[PRINT]
[START]

FIG. 5

1201...ALARM DISPLAY BUTTON TURNED-OFF STATE
1202...ALARM DISPLAY BUTTON TURNED-ON STATE
1203...ALARM UPDATE BUTTON INACTIVE STATE
1204...ALARM UPDATE BUTTON ACTIVE STATE
1213...ALARM UPDATE BUTTON PUSH 1210 / GENERATION OF ALARM CONFIRMATION INFORMATION 1209
1214...ALARM GENERATION 1205 / GENERATION OF ALARM GENERATION INFORMATION 1208
1215...ALARM DELETION BUTTON PUSH AFTER ALARM SELECTION 1211 / GENERATION OF ALARM DELETION INFORMATION 1212
1216...ALARM DISPLAY BUTTON PUSH 1206 / GENERATION OF ALARM CONFIRMATION INFORMATION 1209
1217...ALARM GENERATION 1205 / GENERATION OF ALARM GENERATION INFORMATION 1208
1218...CLOSE BUTTON PUSH 1207 / -
1219...ALARM DISPLAY BUTTON PUSH 1206 / -

---

1205...ALARM GENERATION
1206...ALARM DISPLAY BUTTON PUSH
1207...CLOSE BUTTON PUSH
1208...GENERATION OF ALARM GENERATION INFORMATION
1209...GENERATION OF ALARM CONFIRMATION INFORMATION
1210...ALARM UPDATE BUTTON PUSH
1211...ALARM DELETION BUTTON PUSH AFTER ALARM SELECTION
1212...GENERATION OF ALARM DELETION INFORMATION

| ALARM NO | USER ACTION NO | USER ACTION CONTENT | EXECUTION ORDER | THRESHOLD TIME T2 | ANALYZER STATE NO |
|---|---|---|---|---|---|
| 0001 | 1 | EXECUTE MAINTENANCE A | 1 | 10 MINUTES | 09 |
|  | 2 | EXECUTE MAINTENANCE B | 2 | 15 MINUTES | 01 |
| 0002 | 19 | CLOSE ANALYZER COVER | 1 | 3 MINUTES | 02 |
|  | 17 | PUSH RELEASE KEY OF INTERLOCK MECHANISM | 2 | 3 MINUTES | 08 |
| ... | ... | ... | ... | ... | ... |

FIG. 10

| ALARM NO | THRESHOLD TIME T3 | EXPLANATION OF THRESHOLD TIME T3 |
|---|---|---|
| 0001 | 30 MINUTES | AVERAGE TIME REQUIRED FOR RECOVERY SINCE ANALYZER DEACTIVATION DUE TO CURRENT ABNORMALITY |
| 0002 | 10 MINUTES | AVERAGE TIME REQUIRED FOR RECOVERY SINCE ANALYZER DEACTIVATION DUE TO INTERLOCK MECHANISM |
| 0003 | 0 MINUTE | AVERAGE TIME REQUIRED FOR RECOVERY SINCE ANALYZER DEACTIVATION DUE TO FAILURE OF MOTOR A |
| ... | ... | ... |

FIG. 11

| No. | ALARM GENERATION TIME | LABORATORY NUMBER | ANALYZER NO | ALARM NO | ALARM STATUS | ALARM ELAPSED TIME |
|---|---|---|---|---|---|---|
| 1 | YYYY/MM/DD/HH:MM:SS | 2001 | AAAA | 3458 | ALARM GENERATION | MM:SS |
| 2 | YYYY/MM/DD/HH:MM:SS | 1956 | BBBB | 0001 | ALARM CONFIRMATION COMPLETION | MM:SS |
| 3 | YYYY/MM/DD/HH:MM:SS | 8563 | CCCC | 0002 | NEED TO CONTACT CUSTOMER | MM:SS |

<NOTICE>
MESSAGE: NEED FOR CUSTOMER SUPPORT
SCREEN MANAGEMENT NO:03
NOTICE TIME YYYY/MM/DD/HH:MM:SS

[CLOSE] [SUPPORT COMPLETION] [CLOSE]

AUTOMATIC ANALYZER, REMOTE MAINTENANCE SYSTEM, AND MAINTENANCE METHOD

TECHNICAL FIELD

The present invention relates to an automatic analyzer and a remote maintenance system to execute qualitative analyses and quantitative analyses of specimens such as blood and urine.

BACKGROUND ART

Patent Literature 1 indicates a technique about a remote maintenance system of an automatic analyzer when the analyzer is deactivated in response to alarm generation in the automatic analyzer.

CITATION LIST

Patent Literature

Patent Literature 1: 2011-203197

SUMMARY OF INVENTION

Technical Problem

In a system of Patent Literature 1, when an alarm is generated in an automatic analyzer and a customer is able to handle a cause of the alarm, the automatic analyzer detects that the cause of the alarm is canceled and automatically deletes alarm information from an alarm screen to stop the alarm sound.

In the system of Patent Literature 1, the automatic analyzer continues warning the customer with the alarm sound, regardless of whether the customer has difficulty in handling the alarm. Only when the customer handles the alarm, the alarm sound is stopped. When the customer can handle the alarm by themselves or is handling the alarm, excessive warning to the customer is unnecessary.

A customer may start analysis by mistake, in a state where a safety cover, that is for preventing the injury and infection of hands and fingers caused by a contact with a mechanism portion of the automatic analyzer being opened, the analyzer is deactivated by an interlock mechanism of the analyzer. In this case, it is possible to recover the analyzer by closing the safety cover. When the customer knows the recovery method and can recover the analyzer soon, contacting the customer is unnecessary.

In contrast, when the customer does not know the recovery method, it is necessary for the customer to confirm a recovery procedure by using the recovery procedure displayed on the alarm screen of the analyzer or using an operation manual of the analyzer. Recovery of the analyzer may thus require time. In such a case, when handling of the alarm by the customer is found to require time, it is necessary to contact the customer.

Additionally, when the analysis of the automatic analyzer is brought to a deactivated state due to breakage and failure of the mechanism portion of the analyzer and the alarm is generated, it is difficult for the customer to handle the alarm. To recover the analyzer as soon as possible, it is necessary for the service department to notify the customer of the solution to the alarm immediately after the alarm generation.

Thus, it is necessary to consider whether the service department contacts the customer and when the contact is made in response to a type of the alarm generated in the automatic analyzer and a status of handling the alarm by the customer.

Solution to Problem

A typical procedure that solves the problem is as follows.

An automatic analyzer includes: a display that displays an alarm screen; a computer that generates alarm generation information that indicates an alarm is generated due to abnormality and alarm deletion information indicating that a customer has deleted an alarm displayed on the alarm screen based on the alarm generation information; and an information sharing portion that shares, with an external alarm maintenance system, the alarm generation information and alarm deletion information that are generated by the computer.

For example, when the customer solves the alarm by themselves after the alarm is generated in the automatic analyzer and analysis is brought to a deactivated state, the alarm is deleted from the screen of the automatic analyzer and the automatic analyzer notifies the service department of the alarm deletion information indicating the deletion of the alarm to notify the service department that the alarm has been solved.

When notified of the alarm deletion information within an average time required for the customer to handle the alarm, the service department determines that the customer were able to handle the alarm, and does not contact the customer. In contrast, when not notified of the alarm deletion information even after a time elapses, the service department determines that the customer requires time to handle the alarm and has difficulty in handling the alarm by themselves. The service department then contacts the customer. Additionally, operations of the analyzer by the customer are monitored using analyzer state information. When determining that the operations required to recover the analyzer are not executed, the service department contacts the customer at this determination without waiting for reception of the alarm deletion information.

Another typical means that solves the problem is as follows.

A method of maintaining an automatic analyzer includes: generating alarm generation information that indicates that an alarm generates due to abnormality in a computer of an automatic analyzer; transmitting the generated alarm generation information to an alarm monitoring terminal including a display screen via a server; displaying alarm information on the display screen based on the alarm generation information received by the alarm monitoring terminal; deleting, by a customer, an alarm displayed on an alarm screen of a display of the automatic analyzer; generating alarm deletion information that indicates that a customer has deleted the alarm in the computer based on deletion of the alarm by the customer; transmitting the generated alarm deletion information to the alarm monitoring terminal via the server; and updating the alarm information based on the alarm deletion information received by the alarm monitoring terminal to display the updated alarm information. When time from the alarm generation time exceeds a first threshold time while the alarm monitoring terminal does not receive the alarm deletion information before the first threshold time elapses, a notice of need for customer support is displayed on the display screen. When the alarm monitoring terminal receives the alarm deletion information before the first threshold time elapses and then the first threshold time elapses, the notice is not displayed on the display screen.

Advantageous Effects of Invention

Therefore, only when the customer needs help for recovery of the analyzer, the service department can contact the customer.

Problems, configurations, and advantageous effects of the present disclosure other than the above explanation will be cleared in the following embodiments.

DESCRIPTION OF EMBODIMENTS

Hereafter, one embodiment of an automatic analyzer and an alarm monitoring system according to the present invention are described based on the drawings.

Figure 1:
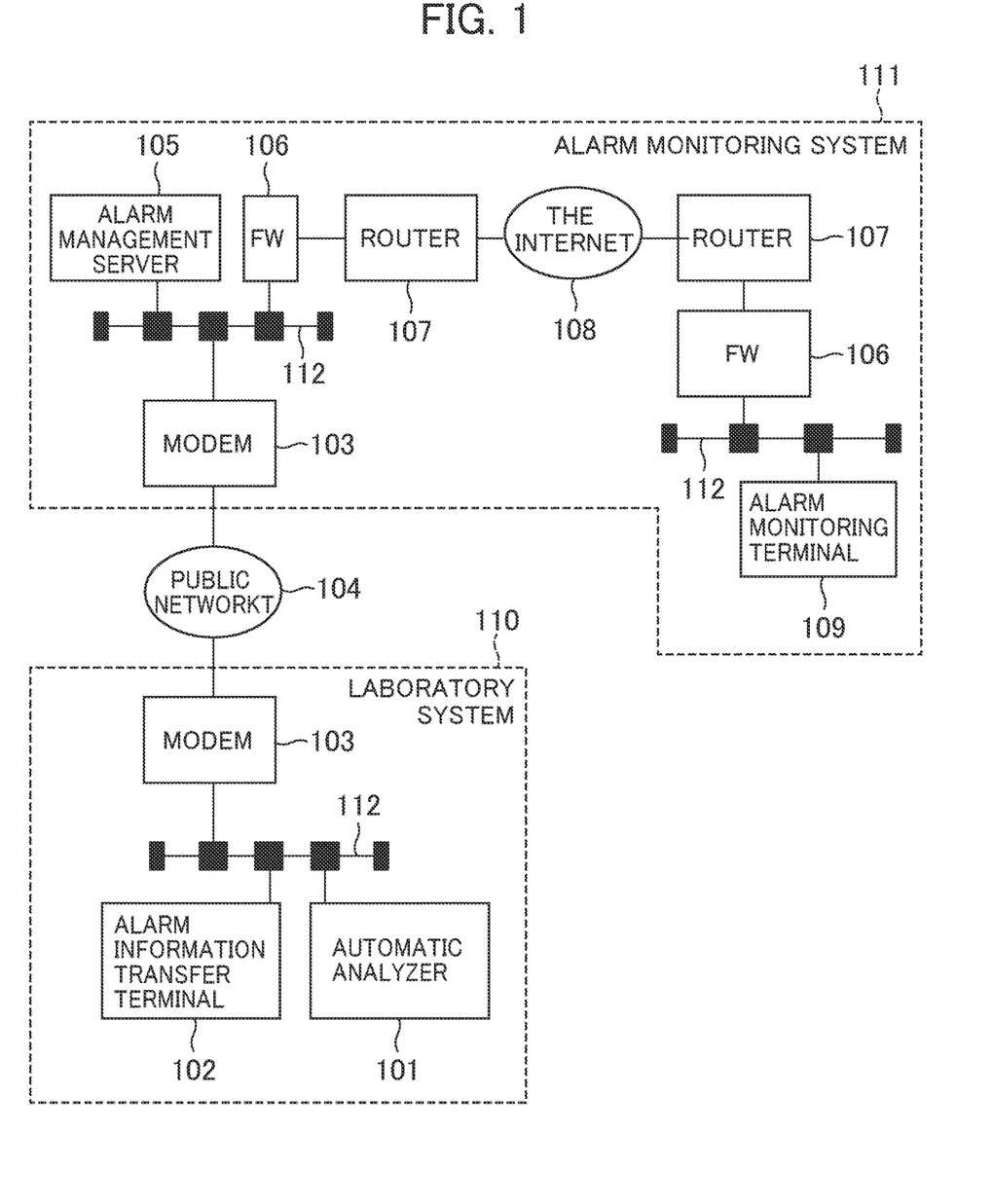
FIG. 1 illustrates an entire configuration of a system.

FIG. 1 illustrates an entire configuration of a system of one example of the automatic analyzer and alarm monitoring system according to the present invention.

In FIG. 1, an automatic analyzer 101 and an alarm information transfer terminal 102 belong to a laboratory system 110 via an LAN (Local Area Network) 112. In FIG. 1, an alarm control server 105 and an alarm monitoring terminal 109 belong to an alarm monitoring system 111 held by a service department via the LAN 112. The laboratory system 110 and alarm monitoring system 111 are connected to each other by a public network 104 via a modem 103 that converts digital signals into analog signals. The alarm control server 105 and alarm monitoring terminal 109 are connected to the Internet 108 via a router 107 and an FW (Firewall) 106. The alarm monitoring system 111 corresponds to a remote maintenance system that remotely monitors the automatic analyzer 101.

Figure 13:
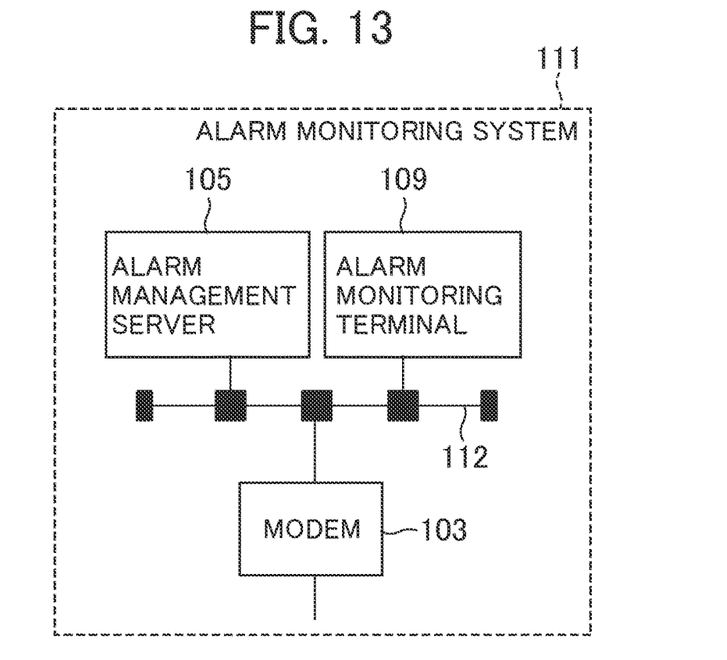
FIG. 13 illustrates another example of the alarm monitoring system.

FIG. 13 illustrates another example of the alarm monitoring system 111. As in FIG. 13, in the alarm monitoring system 111, the alarm control server 105 and alarm monitoring terminal 109 may be connected to each other via a direct LAN 112 instead of the Internet 108.

Figure 2:
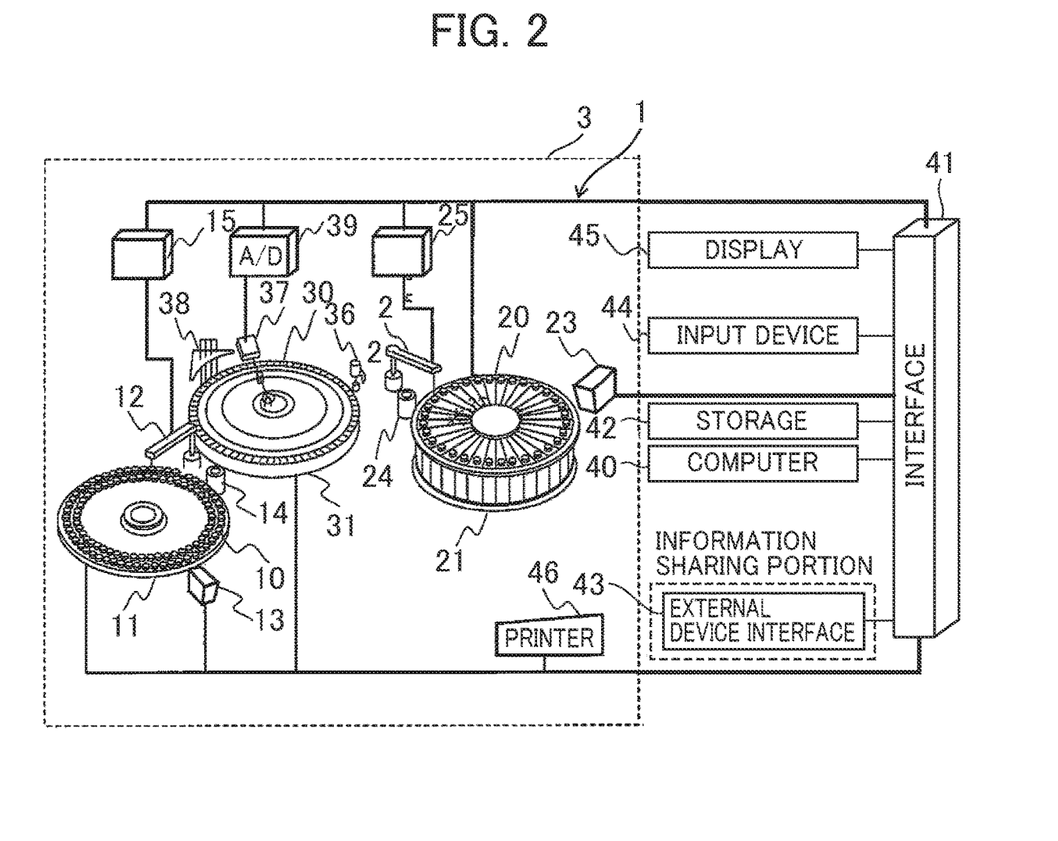
FIG. 2 illustrates an entire configuration of an automatic analyzer.

FIG. 2 illustrates an entire configuration of one embodiment of the automatic analyzer according to the present invention. In FIG. 2, an automatic analyzer 1 includes an analysis unit 3 having a sample disc 11, a reagent disc 21, and a reaction disc 31. Multiple sample containers 10 are mounted to the sample disc 11 in the disc circumferential direction. The reagent disc 21 mounts multiple reagent containers 20, in which reagent are enclosed, in the disc circumferential direction as reagent storehouses in the analyzer. The reaction disc 31 includes multiple reaction containers 30 in the disc circumferential direction. The multiple reaction containers 30 react specimens (samples) with reagents to generate reaction solutions. Each sample container 10 is removably mounted to the sample disc 11. Each reagent container 20 is removably mounted to the reagent disc 21.

A sample dispensing mechanism 12 is installed between the sample disc 11 and reaction disc 31. A reagent dispensing mechanism 22 is installed between the reagent disc 21 and reaction disc 31. The sample dispensing mechanism 12 and reagent dispensing mechanism 22 each include a movable arm and a dispensing nozzle having a pipette nozzle attached to the movable arm.

The sample disc 11 and reagent disc 21 are rotatably structured by unshown driving portions, respectively. The sample disc 11 can rotate to dispose each of the mounted multiple sample containers 10 to a predetermined position in the disc circumferential direction. Similarly, the reagent disc 21 can also rotate to dispose each of the mounted multiple reagent containers 20 to a predetermined position in the disc circumferential direction.

A sample information reader 13 is disposed to a predetermined position in the circumferential direction of the sample disc 11. A sample information reader 23 is disposed to a predetermined position in the circumferential direction of the reagent disc 21. The sample information reader 13 read a sample cord fixed to a recording medium attached to each sample container 10 disposed facing the reader 13. The reagent information reader 23 read a reagent cord fixed to a recording medium attached to each reagent container 20 disposed facing the reader 23. The sample information reader 13 can read each sample cord of the sample containers 10 to detect a mounting state of each sample on the sample disc 11. The reagent information reader 23 can read each reagent cord of the reagent containers 20 to detect amounting state of each reagent on the reagent disc 21.

The sample dispensing mechanism 12 and reagent dispensing mechanism 22 generate, in the reaction containers 30, mixed solutions of the samples and reagents or reaction solutions. To generate reaction solutions, the sample dispensing mechanism 12 inhales a specified amount of a sample from each sample container 10 disposed to a sample inhalation position by rotation of the sample disc 11 and accommodates the inhaled sample in the dispensing nozzle. The sample dispensing mechanism 12 discharges the sample accommodated in this dispensing nozzle into the reaction container 30 disposed to a sample discharge position by rotation of the reaction disc 31 to dispense the sample. In contrast, the reagent dispensing mechanism 22 inhales a specified amount of reagent from the reagent container 20 disposed to a reagent inhalation position by rotation of the reagent disc 21 and accommodates the inhaled reagent in the dispensing nozzle. The reagent dispensing mechanism 22 discharges the reagent accommodated in this dispensing nozzle into the reaction container 30 disposed to a reagent discharge position by rotation of reaction disc 31 to dispense the reagent.

A stirring mechanism 36, a photometry system 37, and a washing mechanism 38 are shifted from each other around the disc of the reaction disc 31 together with the sample dispensing mechanism 12 and reagent dispensing mechanism 22. The stirring mechanism 36 stirs the reaction solution dispensed and generated in each reaction container 30 by the sample dispensing mechanism 12 and reagent dispensing mechanism 22. The reaction solution in each reaction container 30 is thus stirred uniformly to promote the reaction.

The photometry system 37 has a light source (not shown) and an absorption spectrometer (not shown) that face each other across a photometry position through which the reaction containers 30 pass in association with rotation of the reaction disc 31. The photometry system 37 radiates, with measuring light from the light source, each of the reaction containers 30 that store reaction solutions and are disposed in a photometry position between the light source and absorption spectrometer. Then, the photometry system 37 measures the transmitted light by using the absorption spectrometer. Thus, when each reaction container 30 is disposed to the photometry position of the photometry system 37 in response to rotational displacement by intermittent rotation of the reaction disc 31, a transmitted light of the reaction solution in each reaction container 30 is measured. The photometry system 37 may include a diffusion photometer coaxially with the absorption spectrometer or at a different position.

The washing mechanism 38 discards the reaction solutions that have been analyzed for request items from the reaction containers 30 mounted to the reaction disc 31 and washes the insides of the containers in preparation for analyses of new request items. The washing mechanism 38 makes it possible to repeatedly use each of the reaction containers 30 mounted to the reaction disc 31.

Next, the control system and signal processing system in this automatic analyzer 1 are explained.

The control system and signal processing system of the automatic analyzer 1 have a microcomputer (hereinafter also called a computer) 40. A storage 42, an information sharing portion (external device interface) 43, an input device 44, a display 45, and a printer 46 are connected to the microcomputer 40 via an interface 41. The storage 42 includes a hard disk memory and an external memory medium to store work data, measurement result data, analysis result data, etc. The information sharing portion (external device interface) 43 performs information transmission to or from the alarm information transfer terminal 102 or an unillustrated management device (higher computer). The information includes sample information, analysis request items, measurement results, and analysis results. The information transmission executed by the information sharing portion (external device interface) 43 includes transfer and sending of information. As mentioned later, the information sharing portion 43 can share alarm generation information and alarm deletion information with the external alarm monitoring system 111 (alarm maintenance system). The input device 44 has operation portions such as a mouse and a keyboard to execute various command operations and setting operations to the analyzer. The display 45 displays a GUI (Graphical User Interface) used in various command operations and setting operations, measurement results, and analyses results. The printer 46 prints out measurement results and analysis results. The input device 44 and display 45 form a customer interface of the automatic analyzer 1.

Each portion of the analyzer, such as the sample disc 11, the reagent disc 21, the reaction disc 31, the sample information reader 13, the reagent information reader 23, a sample dispensing control portion 15, a reagent dispensing control portion 25, and an A/D converter 39, is connected to the microcomputer 40 via the interface 41. Based on commands from the microcomputer 40, the sample dispensing control portion 15 and reagent dispensing control portion 25 control operations of the sample dispensing mechanism 12 and reagent dispensing mechanism 22 to control dispensing actions of each sample and each reagent, respectively. The A/D converter 39 converts analog detection signals of the absorption spectrometer of the photometry system. 37 into digital signals and supplies the signals to the microcomputer 40.

The automatic analyzer 1 analyzes samples by controlling operations of each portion of the analyzer as follows with the above control system and signal processing system.

The storage 42 stores, as preset data, passwords of operators, calibration results, analysis parameters of analyzable analysis request items, display levels of screens, etc. Before start of analysis (operation) of samples, sample information and an analysis request item of each sample to be analyzed in future are transmitted to the storage 42 via the information sharing portion (external device interface) 43 or input by an operator from the customer interface to the storage 42 and registered to the storage 42. Information about samples on the sample disc 11 and information about reagents on the reagent disc 21 are also registered to the storage 42 in correspondence with mounting positions on the discs based on read outputs of sample cords from the sample information reader 13 and read outputs of reagent cords from the reagent information reader 23.

When the microcomputer 40, in the wait state (standby state) in which sample analyses are not yet executed, receives an operator input of a start command from the customer interface, the microcomputer 40 controls actions of each portion of the analyzer, such as the reagent disc 21, reaction disc 31, sample dispensing mechanism 12, and reagent dispensing mechanism 22. Then, the microcomputer 40 starts analyses of the sample information and request item information that are registered to the storage 42.

When the analysis starts, mounting conditions of samples on the sample disc 11 and reagents on the reagent disc 21 are acquired by the microcomputer 40 and registered to the storage 42 based on each read output from the sample information reader 13 responsive to rotation of the sample disc 11 and from the reagent information reader 23 responsive to rotation of the reagent disc 21.

Specifically, in response to rotation at the start of the operation of the sample disc 11, a mounting position of each of the multiple sample containers 10 mounted circumferentially of the sample disc 11 is defined on the sample disc 11 based on a sample code of each sample container 10 sequentially read by the sample information reader 13. Then, sample information on the sample contained in each sample container 10 mounted on the sample disc 11 is registered to the storage 42 in correspondence with the mounting position on the sample disc 11.

Similarly, in response to rotation at the start of the operation of the reagent disc 21, a mounting position of each of the multiple reagent containers 20 mounted circumferentially of the reagent disc 21 is defined on the reagent disc 21 based on a reagent code of each reagent container 20 sequentially read by the reagent information reader 23. Then, reagent information on the reagent contained in each reagent container 20 mounted on the reagent disc 21 is registered to the storage 42 in correspondence with the mounting position on the reagent disc 21.

Thus, based on the read outputs from the sample information reader 13 and reagent information reader 23, the microcomputer 40 controls rotational displacements of the sample disc 11 and reagent disc 21. Thus, the desired sample and sample container 10 and the desired reagent and reagent container 20 can be disposed to the sample inhalation position of the sample dispensing mechanism 12 and the reagent inhalation position of the reagent dispensing mechanism 22, respectively.

After acquiring the mounting conditions of each sample container 10 on the sample disc 11 and each reagent container 20 on the reagent disc 21, when analyses of the request items registered to the storage 42 include an analysis not yet executed, the microcomputer 40 disposes the sample container 10 containing the sample corresponding to this not-yet executed analysis to a sample inhalation position of the sample dispensing mechanism 12 by rotation of the sample disc 10 to start generating a reaction solution.

In generation of reaction solutions, the microcomputer 40 makes the sample dispensing mechanism 12 inhale a specified amount of a sample according to an analysis parameter of a request item and contain the sample in the nozzle. In that case, the sample liquid amount in this sample container 10 is subtracted by this inhaled specified amount to update the sample liquid amount enclosed in the sample container 10.

When the reaction container 30 that has been washed is disposed to a sample discharge position of the sample dispensing mechanism 12 by intermittent rotation of the reaction disc 31, the microcomputer 40 makes the sample dispensing mechanism 12 discharge the specified amount of the sample contained in the nozzle into this reaction container 30 to dispense the sample. Then, this reaction container 30 and the analysis of the request item of this sample are corresponded to each other. For example, the microcomputer 40 stores this reaction container 30 or the mounting position on the reaction disc 31 in correspondence with the analysis of the request item for this sample registered to the storage 42, and stores a dispensing completion time of this sample to indicate that this sample has been dispensed.

In contrast, when disposing the reaction container 30 corresponding to the analysis of the request item at the reagent dispensing timing to the reagent discharge position of the reagent dispensing mechanism 22 by intermittent rotation of the reaction disc 31, the microcomputer 40 rotatably displaces the reagent disc 11 to dispose, to the reagent inhalation position of the reagent dispensing mechanism 22, the reagent container 20 whose reagent is to be dispensed. The microcomputer 40 then makes the reagent dispensing mechanism 22 inhale a specified amount of the reagent from this reagent container 20 according to an analysis parameter of the request item and contains the inhaled reagent in the nozzle. At this time, the amount of the reagent in this reagent container 20 is subtracted by this inhaled specified amount to update the amount of the reagent contained in the reagent container 20. Then, the reagent liquid amount of the same type of reagent on the reagent disc 11 as the inhaled reagent is subtracted by the inhaled predetermined mount to update the reagent liquid amount (remaining reagent amount) of each type of reagent on the reagent disc 11. The remaining amounts of the reagent containers 20 on the reagent disc 21 are directly measurable by providing a solution amount measurement mechanism at a predetermined position circumferentially of the disc 21.

When the reaction container 30 corresponding to the analysis of the request item of the sample at this reagent dispensing timing is disposed to the reagent discharge position of the reagent dispensing mechanism 22 by intermittent rotation of the reaction disc 31, the microcomputer 40 makes the reagent dispensing mechanism 22 discharge the specified amount of the reagent contained in the nozzle into the reaction container 30 to dispense the reagent. The dispensing completion time of the reagent is then stored in correspondence with the analysis of the request item of this sample registered in the storage 42.

In contrast, the microcomputer 40 analyzes the reaction container 30 on the reaction disc 31 for the request item of the sample. This reaction container 30 has the dispensed sample and reagent and a generated reaction solution and has been identified as being analyzed for the request item.

In this case, at the analysis timing which is set by an analysis parameter of the analysis request item and at which the reaction solution generated in the reaction container 30 is analyzed, the microcomputer 40 disposes that reaction container 30 to the photometry position of the photometry system 37 by intermittent rotation of the reaction disc 31.

When the reaction container 30 is disposed to the photometry position of the photometry system 37, the microcomputer 40 loads a digital detection output of the absorption spectrometer via the A/D converter 39 and calculates measurement and analysis results of the analysis request item of the sample. The measurement and analysis results are then stored in correspondence with the analysis request item of the sample registered to the storage 42.

Thus, when operation is started by the operator input of an operation start command in the automatic analyzer 1 to start analyzing a request item of each sample, sample dispensing completion time information indicating whether each sample has been dispensed, reagent dispensing completion time information indicating whether each reagent has been dispensed, and measurement and analysis results are sequentially additionally stored and accumulated in association with progress of operation in each analysis of request items of the samples registered to the storage 42.

With respect to the reagents enclosed in the reagent containers 20 and mounted and stored to the reagent disc 21, the reagent liquid amount (reagent remaining amount) of each reagent container 20 and the reagent liquid amount (reagent remaining amount) of each reagent type are sequentially updated in association with progress of operation.

Figure 3:
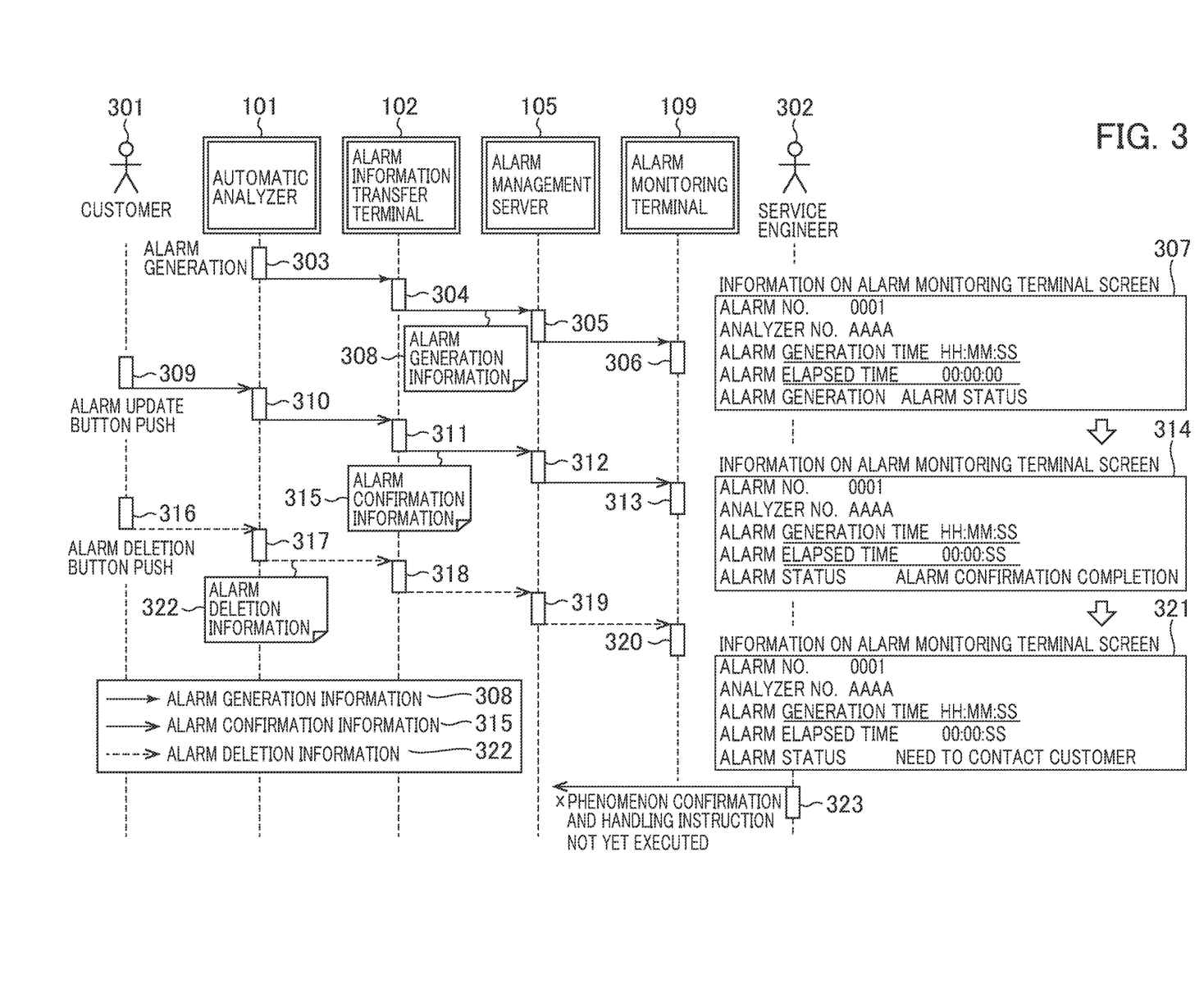
FIG. 3 illustrates a data transfer flow of alarm information.
Figure 4:
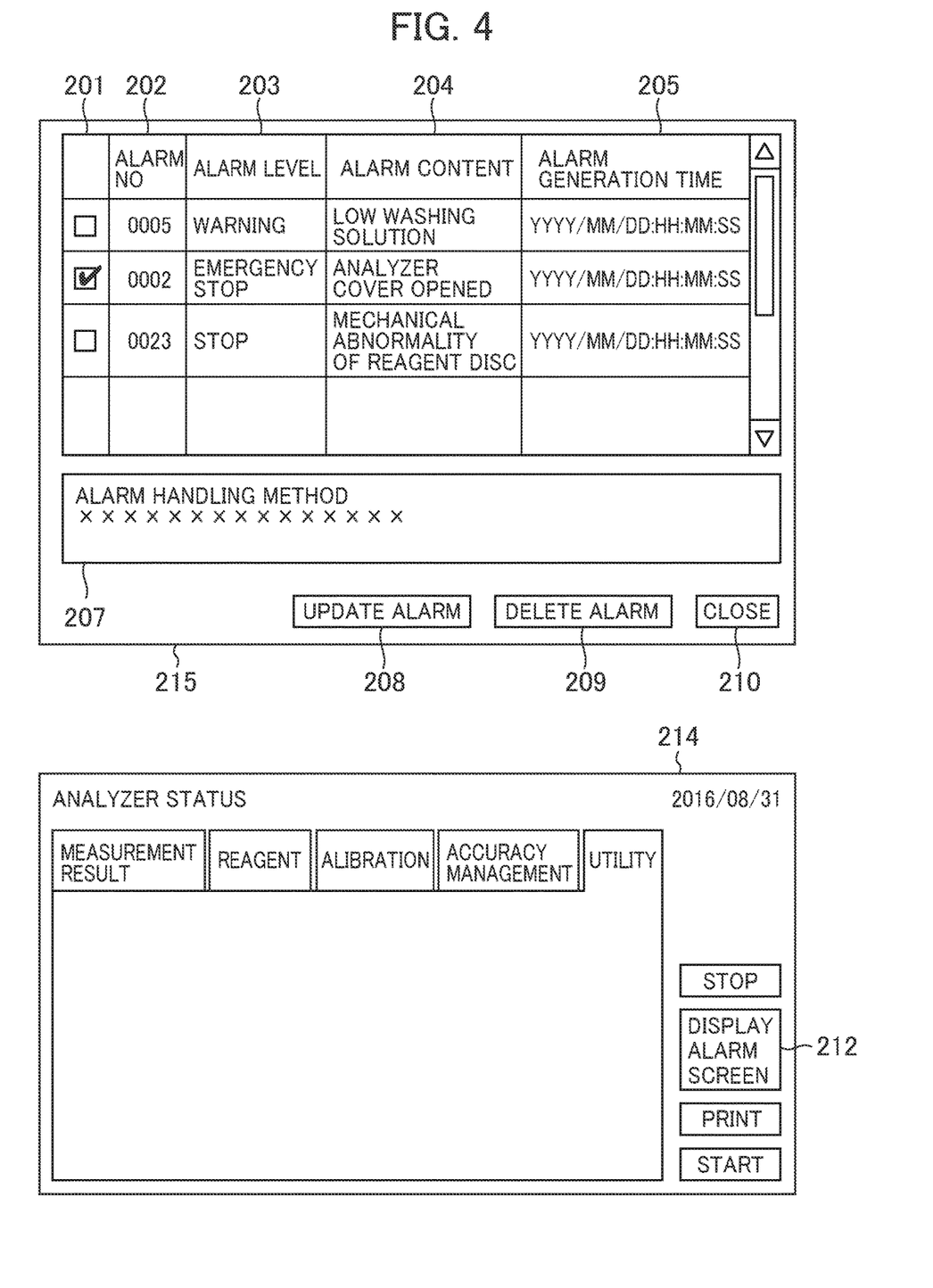
FIG. 4 illustrates an alarm screen of the automatic analyzer.
Figure 5:
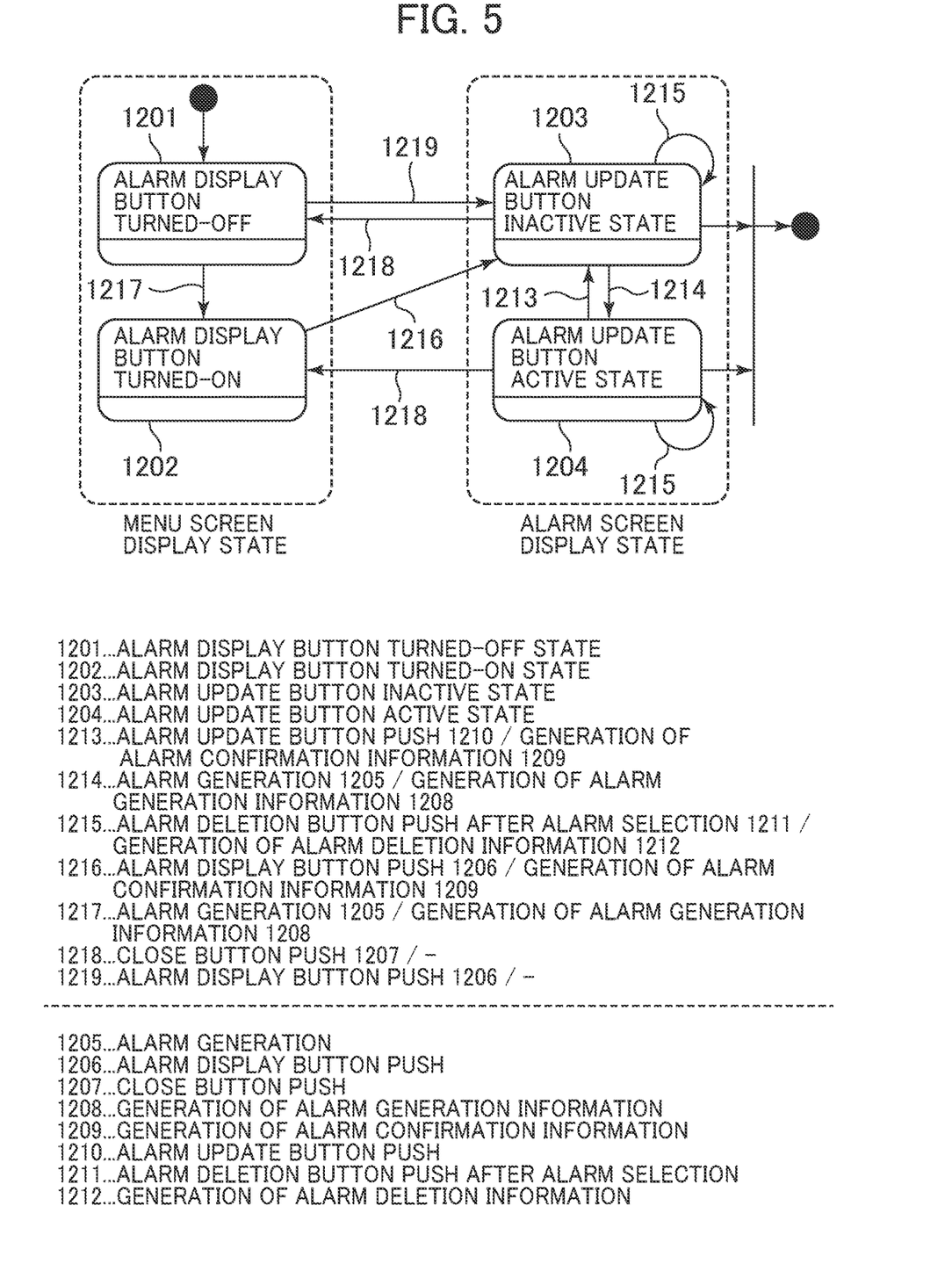
FIG. 5 illustrates timing of generating alarm information of the automatic analyzer.
Figure 6:
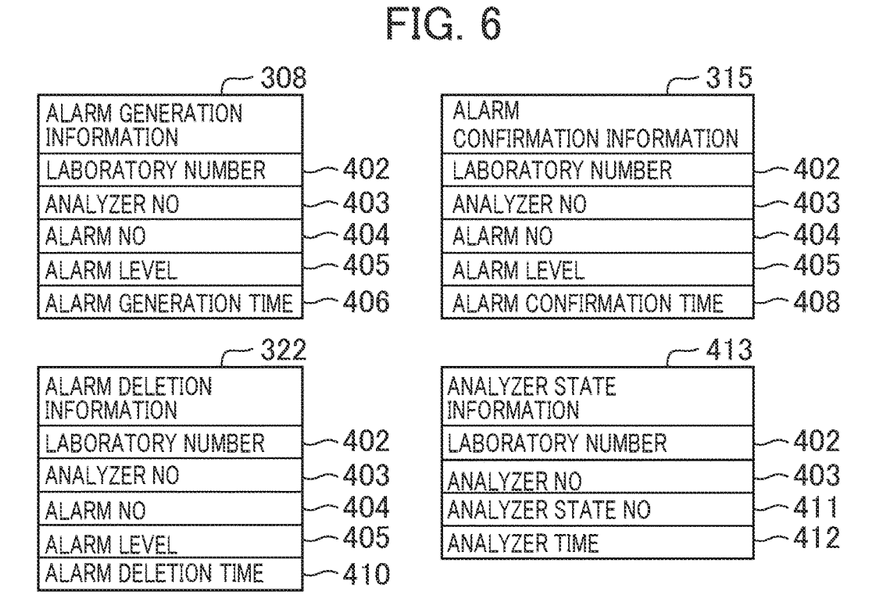
FIG. 6 illustrates definitions of the alarm information and analyzer state information generated by the automatic analyzer.
Figure 7:
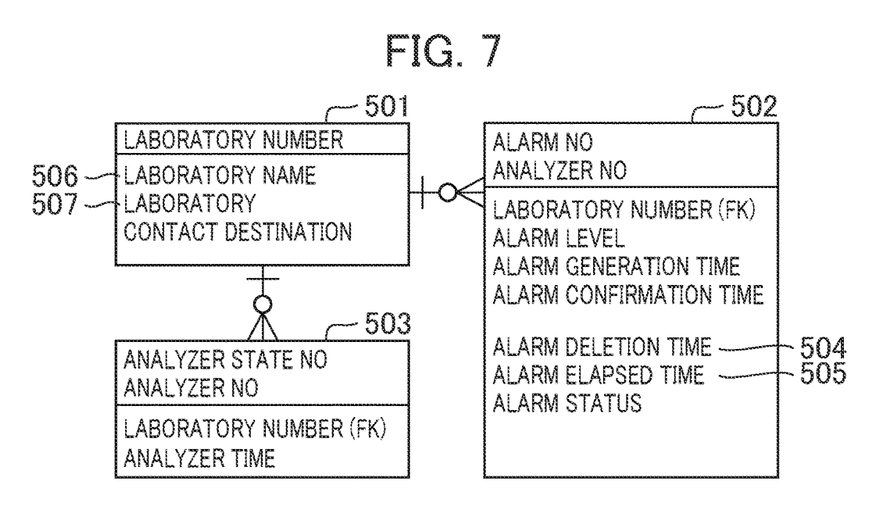
FIG. 7 illustrates a configuration of a database of an alarm management server.

FIG. 3 illustrates a data transfer flow of alarm information. FIG. 4 illustrates an alarm screen of the automatic analyzer 101. FIG. 5 explains timing of generating alarm information in the automatic analyzer 101. FIG. 6 illustrates definitions of the alarm information and analyzer state information generated by the automatic analyzer 101. FIG. 7 illustrates a structure of a database of the alarm control server 105.

First, FIG. 3 is explained. The following various information to be generated is generated by the computer 40 and shared with the alarm information transfer terminal 102 via the information sharing portion (external device interface) 43. The automatic analyzer 101 executes a generation process 303 of alarm generation information 308 that indicates that an alarm is generated due to abnormality of the automatic analyzer 101. The information sharing portion 43 shares this alarm generation information 308 with the alarm information transfer terminal 102. That is, the information sharing portion 43 transfers or sends the alarm generation information 308 to the alarm information transfer terminal 102. The alarm information transfer terminal 102 executes a transfer process 304 to transfer the alarm generation information 308 to the alarm control server 105. The information sharing portion 43 shares this alarm generation information 308 with the alarm information transfer terminal 102. That is, the information sharing portion 43 transfers or sends the alarm generation information 308 to the alarm information transfer terminal 102. The alarm control server 105 executes a storage process 305 to store the alarm generation information 308. The alarm generation information 308 is displayed on the display screen of the external alarm monitoring terminal 109 as display information 307 through a display process 306 of an alarm screen 215 of the automatic analyzer 101.

When an alarm is generated in the automatic analyzer 101, an alarm update button 208 of the alarm screen 215 of the display 45 is activated. When the activated alarm update button 208 is pushed, a generation process 310 of alarm confirmation information 315 is executed to indicate that a customer 301 (user of the analyzer) has confirmed the alarm. The information sharing portion 43 shares this alarm confirmation information 315 with the alarm information transfer terminal 102. That is, the information sharing portion 43 transfers or sends the alarm confirmation information 315 to the alarm information transfer terminal 102. A transfer process 311 is executed to transfer the alarm confirmation information 315 to the alarm control server 105 by the alarm information transfer terminal 102. The alarm control server 105 executes an accumulation process 312 of the alarm confirmation information. A display process 313 of the alarm screen 215 of the automatic analyzer 101 displays display information 314 onto an alarm monitoring terminal screen 109.

When a push operation 309 for the alarm deletion button 209 is executed after the alarm information displayed on the alarm screen 215 of the display 45 is selected from an alarm selection box 201, the automatic analyzer 101 generates alarm deletion information 322 to indicate that the alarm has been deleted from the alarm screen 215. The customer deletes the alarm information of the alarm screen 215 with the alarm deletion button 209 when having solved the cause of the alarm. A generation process 317 of the alarm deletion information 322 is executed to indicate that the customer has deleted the alarm on the alarm screen. The information sharing portion 43 shares this alarm deletion information 322 with the alarm information transfer terminal 102. That is, the information sharing portion 43 transfers or sends the alarm deletion information 322 to the alarm information transfer terminal 102. The alarm information transfer terminal 102 executes a transfer process 318 of the alarm deletion information 322 to the alarm control server 105. The alarm control server 105 executes an accumulation process 319 of the alarm deletion information. A display process 320 of the alarm screen 215 of the automatic analyzer 101 displays display information 321 on the alarm monitoring terminal screen 109. An alarm status 706 of the alarm screen 215 indicates that the alarm has been handled. When the alarm has been handled, a service engineer 302 does not execute a contact 323 with the customer to execute a phenomenon confirmation and a handling instruction.

when any maintenance menu is executed, the automatic analyzer 101 newly generates analyzer state information 413 to indicate an analyzer state in response to a change of the analyzer state such as a change of a sensor state due to opening and closing of the analyzer cover.
The alarm information transfer terminal 102 transfers the analyzer state information 413 to the alarm control server 105.

Thus, the alarm monitoring system 111 receives the alarm generation information, alarm confirmation information, alarm deletion information, etc. that are shared with the information sharing portion 43.

Next, FIGS. 4 and 5 are explained. The alarm screen 215 displayed on the display 45 of the automatic analyzer 101 changes when an alarm screen display button 212 of the menu panel 214 is pushed. A generation process 1208 of the alarm generation information 308 is executed at an alarm generation 1205. The alarm display button 212 enters a turned-on state 1202 from a turned-off state 1201. A generation process 1209 of the alarm confirmation information 315 is executed at an alarm display button push 1206. Alarm numbers 202, alarm levels 203, alarm contents 204, alarm generation times 205, and an alarm handling 207 are displayed on the alarm screen 215. Also when the button is pushed in the alarm display button turned-off state 1201, the transition to the alarm screen 215 is executed. At the alarm generation 1205 while the alarm screen 215 is displayed, the alarm update button 209 enters an active state 1204. When the alarm update button 209 is pushed, the generation process 1209 of the alarm confirmation information 315 is executed. The alarm update button then enters an inactive state 1203. When a pushing operation 1207 of a close button 210 of the alarm screen 215 is executed, the transition to the menu panel 214 is executed. When a pushing operation 1211 of the alarm deletion button 209 is executed after the alarm selection box 201 is selected, a generation process 1212 of the alarm deletion information 322 is executed.

As in FIG. 6 herein, the alarm generation information 308 includes a laboratory number 402, an analyzer number 403, an alarm number 404 assigned for each type of alarm, an alarm level 405, and an alarm generation time 406. The alarm level 405 includes a warning level at which the deactivation of the automatic analyzer 101 does not immediately occur and an emergency stop at which the deactivation of the automatic analyzer 101 occurs.

The alarm confirmation information 315 indicates that the customer has confirmed the alarm in the alarm screen, and includes the laboratory number 402, analyzer number 403, alarm number 404, alarm level 405, and an alarm confirmation time 408.

The alarm deletion information 322 indicates that the customer has deleted the alarm displayed on the alarm screen, and includes the laboratory number 402, analyzer number 403, alarm number 404, alarm level 405, and an alarm deletion time 410.

The analyzer state information 413 includes the laboratory number 402, analyzer number 403, an analyzer state number 411 assigned in response to an analyzer state, and an analyzer time 412. The analyzer time 412 indicates the time at which the analyzer state has changed in the user action needed for handling the alarm.

As in FIG. 7, the alarm control server 105 has a database capable of storing the above alarm generation information 308, alarm confirmation information 315, alarm deletion information 322, and analyzer state information 413. The database includes laboratory information 501, alarm information 502, and analyzer state information 503 (413).

As in FIG. 7, the laboratory information 501 includes the laboratory number 402, a laboratory name 506, and a laboratory contact 407. The alarm information 502 includes an alarm number 502, the analyzer number 403, laboratory number 402, alarm level 405, alarm generation time 406, alarm confirmation time 408, alarm deletion time 410, an alarm elapsed time 504, and an alarm status 505. The analyzer state information 503 (413) includes an analyzer state number 508, the analyzer number 403, laboratory number 402, and analyzer time 412. The alarm control server calculates a time elapsed from the alarm generation time 406, stores the time in the alarm elapsed time 504, and periodically updates the time.

Figure 8:
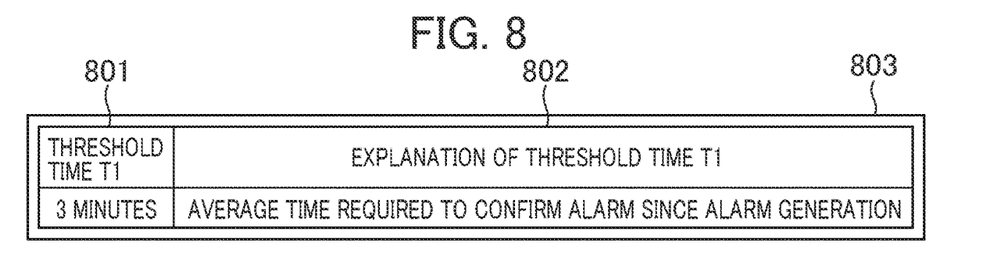
FIG. 8 explains an average time required for a customer to confirm an alarm.

FIG. 8 illustrates a threshold time T1 801 (first threshold time) that indicates an average time required for the customer to confirm an alarm and a data file 803 that defines an explanation 802 of the threshold time T1. As below, the alarm monitoring terminal displays a notice of need for customer support based on this threshold time T1. Thus, when the customer does not confirm an alarm while the threshold time T1 elapses from the alarm generation, it is thought that the customer does not recognize the alarm. The service department is therefore capable of contact to provide a handling instruction. This data file 803 is stored in the alarm monitoring terminal in advance.

Figure 9:
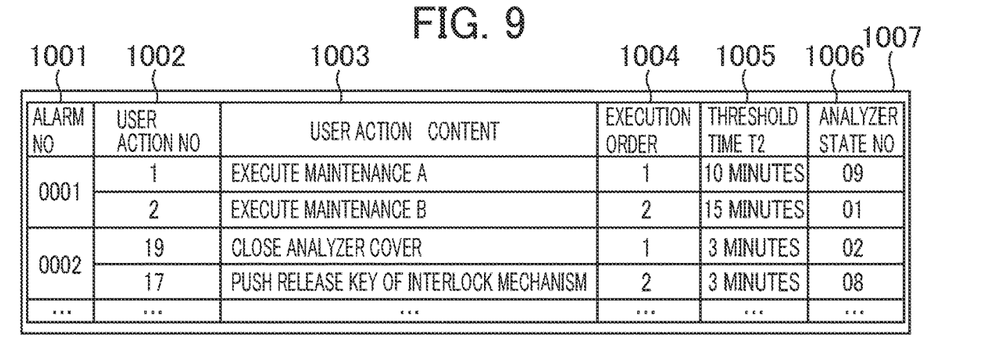
FIG. 9 explains user actions needed for alarm handling.

FIG. 9 illustrates a data file 1007 that defines user action numbers 1002 indicating operations of the automatic analyzer required to handle alarm numbers 1001, user action contents 1003, execution orders 1004 of the user action numbers 1002, threshold times T2 1005 (second threshold times) indicating average times required to execute the user action numbers 1002, and analyzer state numbers 1006 respectively corresponding to the user action numbers. As below, based on each threshold time T2, the alarm monitoring terminal displays the notice of need for customer support on the display screen. It can be thus understood that the customer cannot transit to the next analyzer state even when the threshold time T2 that is set to the user action required to handle the alarm elapses. It can be thus understood that the customer is inexperienced in handling the alarm. The service department can therefore contact the customer to execute phenomenon confirmation and handling instruction. This data file 1007 is stored in the alarm monitoring terminal in advance.

Figure 10:
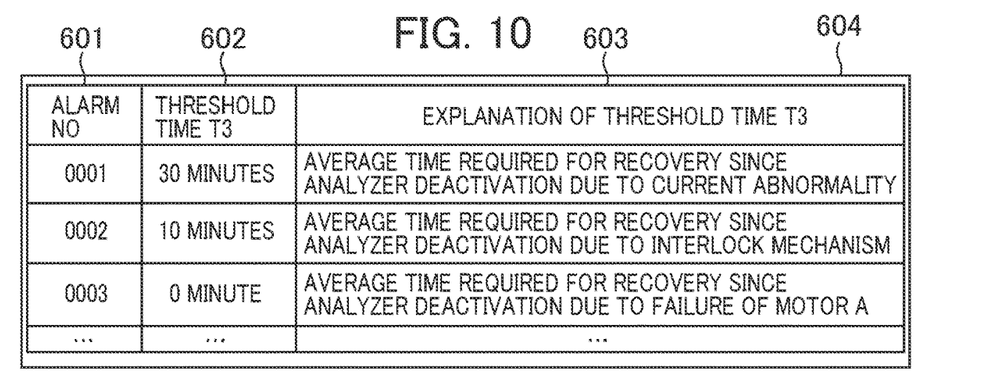
FIG. 10 explains average times required for the customer to handle an alarm.

FIG. 10 has a data file 604 that defines threshold times T3 602 (third threshold times) of average times required for the customer to handle alarm numbers 601 and explanations 603 of the threshold times T3. As below, based on the threshold times T3, the alarm monitoring terminal displays the notice of need for customer support on the display screen. This data file 604 is stored in the alarm monitoring terminal in advance. In FIGS. 8 to 10, average times are set as thresholds. The thresholds do not necessarily use average times. For example, the alarm monitoring terminal may define appropriate times as the thresholds.

Figure 11:
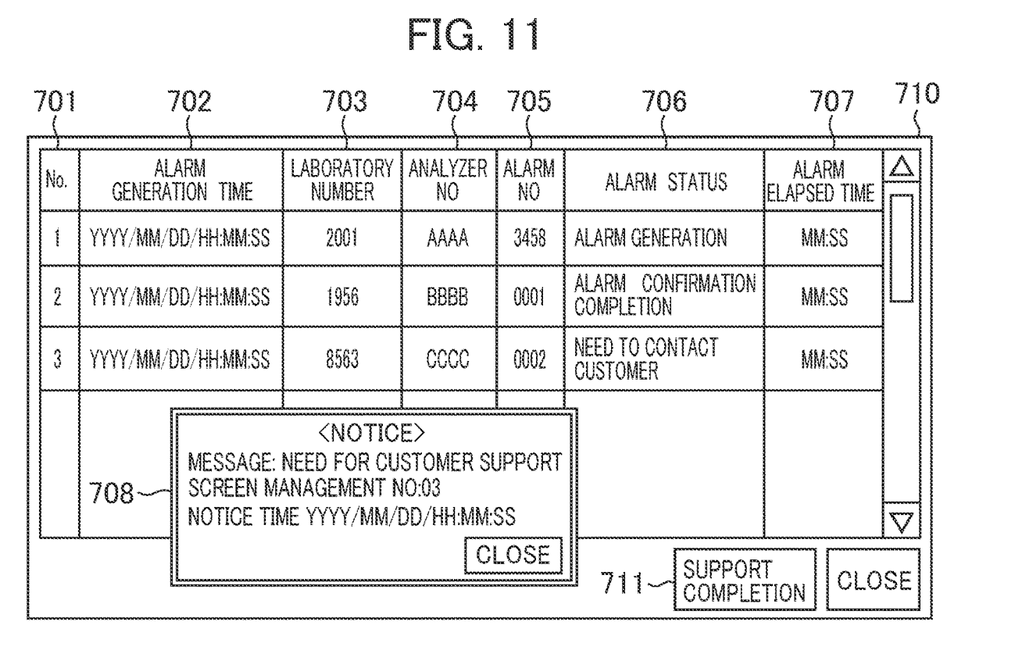
FIG. 11 illustrates a screen of an alarm monitoring terminal.

FIG. 11 illustrates an alarm monitoring terminal screen 710 of the alarm monitoring terminal 109. The alarm monitoring terminal 109 has the alarm monitoring terminal screen 710 displaying screen management numbers 701, alarm generation times 702, laboratory numbers 703, analyzer numbers 704, alarm numbers 705, alarm statuses 706, and alarm elapsed times 207. To indicate that phenomenon confirmation and handling instruction is necessary for the customer when the alarm elapsed time 707 elapses by the threshold time T3 602, the alarm monitoring terminal 109 updates the alarm status 505 of the alarm management server to "need to contact customer," displays "need to contact customer" on the alarm status 706 of the alarm monitoring terminal screen 710, and outputs a notice dialog screen 708 indicating the notice of need for customer support.

A system is provided in which, after the notice dialog screen 708 is displayed on the alarm monitoring terminal screen 710 and the service engineer 302 of the service department is notified of the need for contacting the customer, the service engineer 302 contacts the customer. The service engineer 302 selects the alarm information and pushes a handling completion button 711 after executing phenomenon confirmation and handling instruction for the customer to update the alarm status 706 to "alarm handling completion."

Next, an update process of the alarm status 706 in the alarm monitoring terminal 109 is explained.

Figure 12:
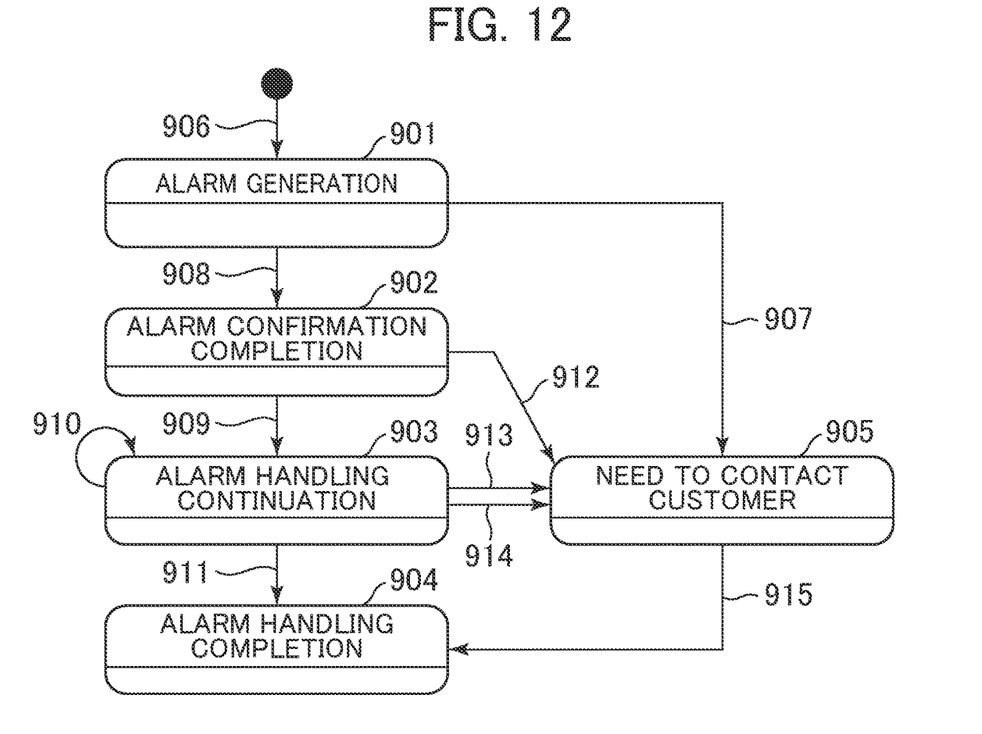
FIG. 12 explains an update process of an alarm status.

FIG. 12 illustrates an update process of the alarm status 706 of the alarm monitoring terminal 109 in detail. The alarm statuses 706 include five types having alarm generation 901, alarm confirmation completion 902, alarm handling continuation 903, alarm handling completion 904, and need to contact customer 905. The alarm status 706 of the alarm control server is updated Through events 906 to 915. The alarm status 706 is displayed on the alarm status of an alarm monitoring terminal 710.

First, the analyzer itself generates an alarm in response to abnormality based on its own sensor etc. The alarm monitoring terminal updates the alarm status 505 to the alarm generation 901 by receiving the alarm generation information 308.

The customer confirms that the alarm has been generated in the analyzer on the alarm screen. The customer makes the analyzer generate alarm confirmation information by pushing the alarm update button of the alarm screen. The alarm monitoring terminal updates the alarm status 505 to the alarm confirmation completion 902 by receiving the alarm confirmation information 315.

The customer performs a user action needed for alarm handling. The alarm monitoring terminal updates the alarm status 505 to the alarm handling continuation 903 by receiving the analyzer state information 413 of the analyzer state number 1006 corresponding to the Kth (K=1) user action number 1002. In addition, 1 is added to K. The alarm monitoring terminal receives the analyzer state information 413 of the analyzer condition number 1006 corresponding the Kth (K=2 to n) user action number 1002. In addition, 1 is added to K. The alarm monitoring terminal repeats the receipt of the analyzer state information 413 until the customer performs n user actions or until K becomes n (910).

The customer executes all the user actions needed for alarm handling to complete the alarm handling. The customer makes the analyzer generate alarm deletion information by pushing the alarm deletion button of the alarm screen. The alarm monitoring terminal updates the alarm status 505 to the alarm handling completion by receiving the alarm deletion information 322 (911).

The above explains the case where the customer can handle the alarm smoothly. The case where the customer cannot handle each status smoothly is explained below.

In the case where the status of alarm generation remains unchanged,
when the threshold time T1 801 elapses from the alarm generation and when the alarm confirmation information 315 is not received, the status is updated to "need to contact customer" 905 (907).

When the status of the alarm confirmation completion remains unchanged, specifically when the analyzer state information 413 of the analyzer state number 1006 corresponding to the Kth (K=1) user action number 1002 is not received at the time at which the threshold time T2 1005 of the Kth (k=1) user action elapses from the reception of the alarm confirmation information 315, the status is updated to "need to contact customer" 905 (912).

When the next user action cannot be entered in each action in the status of the alarm handling continuation, specifically when the Kth (K=2 to n) threshold time T2 1005 elapses after the K−1th (K=2 to n) threshold time T2 1005 elapses, and when the analyzer state information 413 of the analyzer state information number 1006 corresponding to the Kth (K=2 to n) user action number 1002 is not yet received, the status is updated to "need to contact customer" 905 (913).

When the status is not changed to the alarm handling completion in the status such as the alarm handling continuation, specifically when the threshold time T3 602 elapses from the alarm generation after the reception of the analyzer state information 413 of the analyzer state number 1006 corresponding to the Kth (K=n) user action number 1002, and when the alarm deletion information 322 is not yet received, the status is updated to the "need to contact customer" 905 (914).

Even when the customer cannot handle the alarm by themselves, the customer can receive the handling instruction from the service department by the above "need to contact customer." Finally, the customer can handle the alarm. In this case, the alarm on the alarm monitoring terminal screen is selected to push the handling completion button 711 at the service department. Thereby, the alarm status 505 can be updated to the alarm handling completion 904 (915).

When the analyzer is deactivated to generate an alarm due to abnormality of the automatic analyzer, but the customer is executing the operation needed for the analyzer recovery, and is expected to handle the alarm by themselves, and when the customer has handled the alarm by themselves, it is preferable that the service department does not contact the customer. In contrast, when it is determined that the customer does not execute the operation needed for the analyzer recovery and that it is likely to require time for the customer to handle the alarm by themselves, the service department contacts the customer at this determination. When the customer has difficulty in handling the alarm by themselves, a system is provided to make the service department contact the customer immediately after the alarm generation. The service department can thus contact the customer only when the customer needs help to recover the analyzer.

Hereafter, the advantageous effects are explained. As above, the automatic analyzer includes the computer that generates the alarm deletion information indicating that the customer has deleted the alarm displayed on the alarm screen based on the alarm generation information and the information sharing portion that shares the alarm deletion information generated by the computer with the external alarm monitoring system (computer maintenance system). The customer can cancel the alarm without receiving the contact from the service department.

The alarm monitoring terminal displays alarm information onto the display screen based on the received alarm generation information and updates the alarm information based on the received alarm deletion information and displays the updated alarm information. Thus, the service department does not need to contact the customer when the customer cancels the alarm by themselves.

The alarm information displayed on the display screen by the alarm monitoring terminal displays the alarm status that distinguishes the alarm generation from the alarm handling completion. The alarm monitoring terminal updates the alarm status to the alarm handling completion based on the received alarm deletion information. The service department can perceive cancellation of the alarm from the alarm status.

The alarm generation information includes an alarm generation time that indicates the time of alarm generation. The alarm monitoring terminal stores the first threshold times in advance. When time from the alarm generation time exceeds the first threshold time, the alarm monitoring terminal preferably displays the notice of need for customer support on the display screen. It is preferable that, when receiving the alarm deletion information before the first threshold time elapses, the alarm monitoring terminal does not display this notice even when the first threshold time elapses. Particularly, by displaying this notice on the display screen, the service department can certainly contact the customer who has spent a predetermined time from alarm generation even when the department overlooks the status.

The alarm screen preferably has the alarm deletion button. The computer preferably generates the alarm deletion information based on push of the alarm deletion button. The alarm information transfer terminal preferably transfers the alarm deletion information to the external alarm monitoring system. The information on alarm cancellation can be easily transmitted to the service department by providing the alarm deletion button.

The computer preferably generates the alarm confirmation information indicating that the customer has confirmed the alarm on the alarm screen. The alarm information transfer terminal preferably transmits the alarm confirmation information generated by the computer to the alarm monitoring system. Thereby, the service department can easily perceive that the customer has recognized the alarm generation.

The alarm monitoring terminal preferably displays alarm information onto the display screen based on the received alarm generation information to update the alarm information based on the received alarm confirmation information and alarm deletion information and display the updated alarm information. Thereby, the service department can easily perceive that the customer has recognized the alarm generation.

The alarm status that distinguishes among at least alarm generation, alarm confirmation completion, and alarm handling completion is preferably displayed in the alarm information displayed on the display screen by the alarm monitoring terminal. The alarm monitoring terminal preferably updates the alarm status to the status of alarm confirmation completion based on the received alarm confirmation information and the alarm status to the status of alarm handling completion based on the received alarm deletion information. Thereby, the service department can easily perceive whether the customer has recognized the alarm or handled the alarm.

The alarm confirmation information preferably includes an alarm confirmation time that indicates the time at which the customer has confirmed the alarm by pushing the alarm update button. The alarm monitoring terminal preferably stores the second threshold times in advance. When time from the alarm generation time exceeds the second threshold time, the alarm monitoring terminal preferably displays the notice of need for customer support on the display screen. Thereby, the service department can immediately provide a handling instruction to the customer before the time in FIG. 10 elapses.

The automatic analyzer includes the computer that generates analyzer state information indicating an analyzer state and the alarm information transfer terminal that transfers the analyzer state information generated by the computer to the alarm monitoring system.

It is preferable that the alarm monitoring terminal displays alarm information on the display screen based on the received alarm generation information, updates the alarm information based on the received analyzer state information and alarm deletion information, and displays the updated alarm information. Thereby, the service department can easily perceive the action state of the customer.

The alarm information displayed on the display screen by the alarm monitoring terminal preferably displays the alarm status that distinguishes among at least alarm generation, alarm handling continuation, and alarm handling completion. The alarm monitoring terminal preferably updates the alarm status to the status of alarm handling continuation based on the received analyzer state information and to the status of alarm handling completion based on the received alarm deletion information. Thereby, the service department can easily perceive the action state of the customer.

The analyzer state information preferably includes an analyzer time that indicates the time at which the analyzer state changes during the customer action needed for handling the alarm. It is preferable that the alarm monitoring terminal preferably stores a third threshold time in advance and displays the notice of need for customer support on the display screen when time from the analyzer time exceeds the third threshold time. Thereby, the service department can immediately provide a handling instruction to the customer before the time in FIG. 10 elapses.

LIST OF REFERENCE SIGNS

101 . . . Automatic analyzer
102 . . . Alarm information transfer terminal
105 . . . Alarm management server
109 . . . Alarm monitoring terminal
111 . . . Alarm monitoring system
308 . . . Alarm generation information
315 . . . Alarm confirmation information
322 . . . Alarm deletion information

The invention claimed is:

1. A remote maintenance system comprising: an automatic analyzer including: a display that displays an alarm screen; a computer programmed to generate alarm generation information that indicates an alarm due to an abnormality and alarm deletion information indicating that a customer has deleted an alarm displayed on the alarm screen based on the alarm generation information; and an information sharing portion that shares the alarm generation information generated by the computer and the alarm deletion information with an external alarm maintenance system, wherein the external alarm maintenance system comprises an alarm monitoring terminal that includes a display and that receives the alarm generation information and the alarm deletion information, wherein the alarm monitoring terminal displays alarm information on the display based on the received alarm generation information and updates and displays the alarm information based on the received alarm deletion information, wherein the alarm generation information includes an alarm generation time indicating a time of generation of the alarm, wherein the alarm monitoring terminal stores a first threshold time, wherein upon the computer determining the time from the alarm generation time exceeds the first threshold time, display a notice indicating a need for customer support on the display, and wherein upon the computer receiving the alarm deletion information before the first threshold time elapses, the alarm monitoring terminal does not display the notice on the display even when the first threshold time elapses.

2. The remote maintenance system according to claim 1, wherein alarm information displayed on the display by the alarm monitoring terminal indicates an alarm status that distinguishes between at least alarm generation and alarm handling completion, and the alarm monitoring terminal updates the alarm status to a status of alarm handling completion based on the received alarm deletion information to display the updated status.

3. The remote maintenance system according to claim 1, wherein the alarm monitoring terminal stores in advance the first threshold time for each item of the alarm.

4. The remote maintenance system according to claim 1, wherein the alarm screen of the automatic analyzer has an alarm deletion button,
wherein the computer generates the alarm deletion information based on a push of the alarm deletion button, and
the information sharing portion transmits the alarm deletion information to the external alarm maintenance system.

5. A remote maintenance system comprising: an automatic analyzer, comprising: a display that displays an alarm screen; a computer that generates alarm generation information that indicates an alarm is generated due to an abnormality and alarm deletion information indicating that an alarm displayed on the alarm screen based on the alarm generation information has been deleted; and an information sharing portion that shares the alarm generation information generated by the computer and the alarm deletion information with an external alarm maintenance system; wherein the computer generates alarm confirmation information that indicates that a customer confirms the alarm on the alarm screen, wherein the information sharing portion transfers the alarm confirmation information generated by the computer to the external alarm maintenance system, wherein the external alarm maintenance system includes an alarm monitoring terminal that includes a display and that receives the alarm generation information, analyzer state information, and the alarm deletion information that are transferred from the information sharing portion, and wherein the alarm monitoring terminal displays alarm information on the display of the alarm monitoring terminal based on the received alarm generation information and updates and displays the alarm information based on the received analyzer state information and the received alarm deletion information.

6. The remote maintenance system according to claim 5, wherein alarm information displayed on the display of the alarm monitoring terminal indicates an alarm status that distinguishes among at least alarm generation, alarm confirmation completion, and alarm handling completion, and the alarm monitoring terminal updates the alarm status to a status of alarm confirmation completion based on the received alarm confirmation information and updates the alarm status to a status of alarm handling completion based on the received alarm deletion information to display the updated status.

7. The remote maintenance system according to claim 5, wherein the alarm confirmation information includes an alarm confirmation time that indicates a time at which the customer confirms the alarm by pushing an alarm update button, the alarm monitoring terminal stores a second threshold time in advance, and when time from the alarm generation time exceeds the second threshold time, the alarm monitoring terminal displays a notice of need for customer support on the display of the alarm monitoring terminal.

8. A remote maintenance system comprising: an automatic analyzer, comprising: a display that displays an alarm screen; a computer that generates alarm generation information that indicates an alarm is generated due to an abnormality and alarm deletion information indicating that a customer has deleted the alarm displayed on the alarm screen based on the alarm generation information; and an information sharing portion that shares the alarm generation information generated by the computer and the alarm deletion information with an external alarm maintenance system; wherein the computer generates analyzer state information that indicates an analyzer state, wherein the information sharing portion transfers the analyzer state information generated by the computer to the external alarm maintenance system, wherein the external alarm maintenance system includes an alarm monitoring terminal that includes a display and that receives the alarm generation information, the analyzer state information, and the alarm deletion information that are transferred from the information sharing portion, wherein the alarm monitoring terminal displays alarm information on the display of the alarm monitoring terminal based on the received alarm generation information and updates and displays the alarm information based on the received analyzer state information and the received alarm deletion information, wherein alarm information displayed on the display of the alarm monitoring terminal by the alarm monitoring terminal indicates an alarm status that distinguishes among at least alarm generation, alarm handling continuation, and alarm handling completion, and wherein the alarm monitoring terminal updates the alarm status to a status of alarm handling continuation based on the received analyzer state information and updates the alarm status to a status of alarm handling completion based on the received alarm deletion information to display the updated alarm status.

9. The remote maintenance system according to claim 8, wherein the analyzer state information includes an analyzer time indicating a time at which an analyzer state changes in a customer action required for alarm handling, the alarm monitoring terminal stores a third threshold time in advance, and when time from the analyzer time exceeds the third threshold time, the alarm monitoring terminal displays a notice of need for customer support on the display of the alarm monitoring terminal.

10. The remote maintenance system according to claim 9, wherein the alarm monitoring terminal stores in advance the third threshold time for each item of the customer action.

11. A maintenance method for an automatic analyzer comprising: generating alarm generation information, by a computer of the automatic analyzer, that indicates that an alarm is generated due to an abnormality; transmitting the alarm generation information to an alarm monitoring terminal including a display screen via a server; displaying alarm information on the display screen based on the alarm generation information received by the alarm monitoring terminal; deleting, by a customer, the alarm that is displayed on an alarm screen of a display of the automatic analyzer; generating alarm deletion information that indicates that the customer has deleted the alarm based on deletion of the alarm by the customer; transmitting the alarm deletion information to the alarm monitoring terminal via the server; and updating the alarm information based on the alarm deletion information received by the alarm monitoring terminal to display the updated alarm information, wherein when time from an alarm generation time exceeds a first threshold time while the alarm monitoring terminal does not receive the alarm deletion information before the first threshold time elapses, the alarm monitoring terminal displays a notice of need for customer support on the display screen, and when the alarm deletion information is received before the first threshold time elapses and then the first threshold time elapses, the notice is not displayed on the display screen.

12. The maintenance method for an automatic analyzer according to claim 11, comprising having the alarm monitoring terminal store in advance the first threshold time for each item of the alarm.

* * * * *